(12) United States Patent
Mermet et al.

(10) Patent No.: US 8,679,419 B2
(45) Date of Patent: Mar. 25, 2014

(54) STERILE PACKING AND STERILIZATION METHOD USING THIS PACKING

(75) Inventors: Emeric Mermet, Grenoble (FR); Thomas Dubois, Echirolles (FR)

(73) Assignee: Becton Dickinson France, Le Pont de Claix (FR)

( * ) Notice: Subject to any disclaimer, the term of this patent is extended or adjusted under 35 U.S.C. 154(b) by 491 days.

(21) Appl. No.: 12/996,640

(22) PCT Filed: Jun. 9, 2008

(86) PCT No.: PCT/IB2008/002514
§ 371 (c)(1),
(2), (4) Date: Feb. 10, 2011

(87) PCT Pub. No.: WO2009/150486
PCT Pub. Date: Dec. 17, 2009

(65) Prior Publication Data
US 2011/0123396 A1    May 26, 2011

(51) Int. Cl.
*A61L 2/00*    (2006.01)
*B29D 22/00*    (2006.01)
*B65B 41/18*    (2006.01)

(52) U.S. Cl.
USPC ............ 422/294; 428/34.1; 428/221; 53/170

(58) Field of Classification Search
USPC ............ 422/294; 428/34.1, 221; 53/432, 460, 53/79, 111 R, 170, 512
See application file for complete search history.

(56) References Cited

U.S. PATENT DOCUMENTS

2005/0042398 A1 *   2/2005   Vanhamel et al. ........... 428/34.2

* cited by examiner

*Primary Examiner* — Monzer R Chorbaji
(74) *Attorney, Agent, or Firm* — Hoffmann & Baron, LLP

(57) ABSTRACT

This sterile packing (1) includes:—a container (3) for containing at least an object (2) to be sterilized by at least a sterilizing fluid, said container (3) including at least a first opening (10);—at least one first membrane (16) made in a material porous to the sterilizing fluid but non-porous with respect to microbial contamination, said at least one first membrane (16) being sealed at said at least a first opening (10) of the container (3), after filling of the container (3) with the object (2) so as to close said at least a first opening (10);—at least one second membrane (22) made in a flexible and airtight material, said second membrane (22) being sealed at said at least first opening (10) of the container (3), after installation of said first membrane (16), the sealing of said second membrane (22) being carried out at a pressure higher than the atmospheric pressure, so that said second membrane (22) is curved when the packing (1) is brought back to the atmospheric pressure.

13 Claims, 2 Drawing Sheets

STERILE PACKING AND STERILIZATION METHOD USING THIS PACKING

The present invention concerns a sterile packing and a sterilization method using this packing.

Some activities involve transporting sterile parts or components in sterile packing. This is the case in particular for the component parts of syringes, which must be transported between the production site and an assembly site, to form the syringe, and fill the syringe bodies.

A known sterilization method used for syringe parts consists of placing these parts in packings made of a flexible and airtight material, then exposing these packings thus filled to gamma rays. This method has the drawback, for the syringe manufacturer, of having to pack the non-sterilized parts in non-sterile packings, then to transmit these packings to a service provider specialized in this type of sterilization, which, after sterilization, transmits these packings to the purchaser of the parts, for assembly and/or filling of the syringes. The use of a specialized sub-contractor of this type constitutes a notable constraint for the syringe manufacturer.

Another known sterilization method in such an application uses water vapor to sterilize the parts and their packing. This sterilization method is preferred to the radiation sterilization method because it is well-received by the pharmaceutical industry using the syringes, or even required by some users, or is also made obligatory by the nature or material of the packed parts or components. There are not, however, packings making it possible to ensure the perfect performance of sterilization during the sterilization method and, after transport, the perfect preservation of the integrity of the packing all the way to the end user.

The present invention aims to resolve the abovementioned drawbacks.

Its primary aim is therefore to provide a packing making it possible to ensure the perfect performance of a sterilization, in particular using water vapor, of said parts or components, to ensure a perfect preservation of sterility during transport and storage of this packing, and to immediately detect any loss of integrity of the packing and therefore any loss of sterility thereof.

Another aim of the invention is to provide a sterilization method using this packing, which makes it possible to sterilize, in particular by water vapor, said parts or components while ensuring the perfect performance of the sterilization thereof.

The term "object" will be used below generically to generally designate one or several parts or components to be packed; this term must be understood in the broadest sense, covering all types of part(s), product(s) or component(s), and in particular all component parts of syringes.

To achieve the abovementioned objective, the packing according to the invention comprises:
  a container for containing at least one object to be sterilized by at least one sterilizing fluid, said container including at least one first opening;
  at least one first membrane made in a material porous to the sterilizing fluid but non-porous with respect to microbial contamination, said at least one first membrane being sealed at said at least one first opening of the container, after filling of the container with the object(s) to be packed, so as to close said at least one first opening;
  at least one second membrane made in a flexible and airtight material, said second membrane being sealed at said at least one first opening of the container, after installation of said first membrane, the sealing of said second membrane being carried out at a pressure higher than the atmospheric pressure, so that said second membrane is curved when the packing is brought back to the atmospheric pressure.

The sterilization and packing method according to the invention comprises the steps consisting of:
  filling the abovementioned container with said at least one object to be sterilized;
  sealing said at least one first membrane on said at least one first opening;
  simultaneously or not, sterilizing this assembly using said sterilization fluid and putting this assembly under a pressure higher than the atmospheric pressure;
  sealing said at least one second membrane on said at least one first opening while said pressure higher than the atmospheric pressure is maintained, such that said second membrane is curved when the packing is brought back to the atmospheric pressure.

The invention thus consists of using at least one first membrane whereof the porosity allows a sufficient diffusion of the sterilization fluid inside the container and around the object(s) contained in the container; the tight sealing of this or these first membrane(s) on the container makes it possible to preserve the integrity of the sterilization done to the object, of the internal wall of the container and the internal wall of this or these first membrane(s).

Tight sealing of said second membrane(s) on the container while the assembly is placed under a pressure higher than the atmospheric pressure makes it possible that, when the packing is brought back to the atmospheric pressure, said second membrane(s) is/are curved. This curving indicates the absence of escaped air from inside the packing, and therefore indicates the sterility of said packing.

The packing and the method according to the invention thus have the determining advantages of enabling effective sterilization of objects by the sterilization fluid, perfectly protecting the packed object(s) with regard to the environment, and making it possible to immediately indicate any loss of integrity, and therefore sterility, of the packing.

The material of said at least one first membrane comprises pores whereof the size can go from 2 to 15 microns and a Log Reduction Value (as defined in the ASTM F-1608 standard) greater than or equal to 3. This can be a film marketed by the company Du Pont De Nemours under the TYVEK® brand, references 1073B, 2FS or 1059B, or the complex marketed by the company WIPAK under the WIPAK® brand, references Paper 80B or Paper 120B.

Preferably, the container comprises a second opening covered by said first and second membranes and includes a connection ring for connection to a sterile enclosure in which the object(s) to be packed is/are intended to be transferred, this connection ring being connected to said second opening.

The connection of the container to said sterile enclosure for the transfer of the object(s) into this enclosure can, thanks to this ring, be done under the best conditions, the transfer being perfectly aseptic and ensuring maintained sterility during its progress.

Said connection ring can in particular be of the type described in documents U.S. Pat. Nos. 6,571,540 and 6,817,143.

The container advantageously comprises an envelope able to contain the connection ring and forming a seat for sealing of said at least one first membrane.

According to one embodiment of the packing according to the invention, the container comprises at least one third opening located at an end opposite the end whereon said first opening is located, a second of said at least one first membrane being sealed to said at least one third opening of the container, after filling of the container with the object(s) in order to close this at least one third opening.

The container thus includes two said first membranes, on two opposite ends, which ensures perfect penetration and circulation of the sterilization fluid inside the container and around the object(s) to be sterilized.

The packing can include a second said second membrane sealed on said at least one third opening of the container, after filling of the container with the object(s), the sealing of this said second membrane being done at a higher pressure than the atmospheric pressure, such that this said second membrane sealed on said third opening is curved when the packing is returned to the atmospheric pressure.

The container can have any suitable shape, and in particular a truncated or truncated pyramid shape, in which case said at least one first opening, or, when said connection ring is present, said second opening, is located at the small cross-section end of this container while said third opening is located at the base of this container.

This third opening thus has a significant surface, making it possible to obtain a perfect sterilization.

In this case of a third opening at the base of the container, the container comprises a base making it possible, when the container is placed on a surface, to draw aside, relative to this surface, the membrane closing this third opening.

Preferably, the packing according to the invention comprises at least one lid able to cover one said second membrane, in the curved state of this second membrane.

This lid thus ensures the protection of this second membrane with regard to a risk of crushing or exertion of stretching stresses on this membrane.

Each lid is preferably completely or partially transparent, in order to allow the visualization of the shape of the second membrane through it.

The integrity of this second membrane can thus be verified without it being necessary to remove this lid.

The container can comprise a discharge conduit for the object(s), able to be engaged through the opening of this container serving to discharge this or these object(s) outside this container.

This discharge conduit makes it possible to guide the discharge of the objects and/or to isolate these objects relative to the environment during this discharge. In particular, when the discharge opening is equipped with said connection ring, said discharge conduit makes it possible to isolate the objects relative to the base to which this ring is connected. This discharge conduit can in particular be in the form of a foldable horn.

Moreover, at least one said first membrane can be formed by a plurality of layers.

This plurality of layers minimizes the risk of a loss of integrity of the packing if a hole appears in one layer. Moreover, the risk of having aligned holes decreases as the number of layers increases.

The container is preferably rigid.

This rigidity makes it possible to preserve the integrity of these objects with regard to mechanical stresses likely to be exerted on them, in particular during the transport of objects, which is necessary when these objects are likely to be deformed or damaged under the prolonged exertion of such mechanical stresses, as is the case for example for syringe plungers. This rigidity also has the advantage of granting a fixed shape to the set of objects, optimized for a homogenous exposure to the sterilization fluid, which is a crucial parameter for the performance of a sterilization using such a sterilization fluid, in particular through water vapor. In other words, the rigid container makes it possible to eliminate any pile of objects which would be made possible with a flexible container, causing a risk of the sterilization fluid not sufficiently penetrating to the center of this pile to ensure the required sterilization. The rigidity of the container also has the advantage of making it possible to increase the capacity of a packing relative to the maximum capacity which a known flexible packing can have, and to facilitate the treatments and manipulations done by the operators.

The invention will be well understood, and other characteristics and advantages thereof will appear, in reference to the appended diagrammatic drawing, showing, as a non-limiting example, one preferred embodiment of the sterile packing it concerns.

Figure 6:
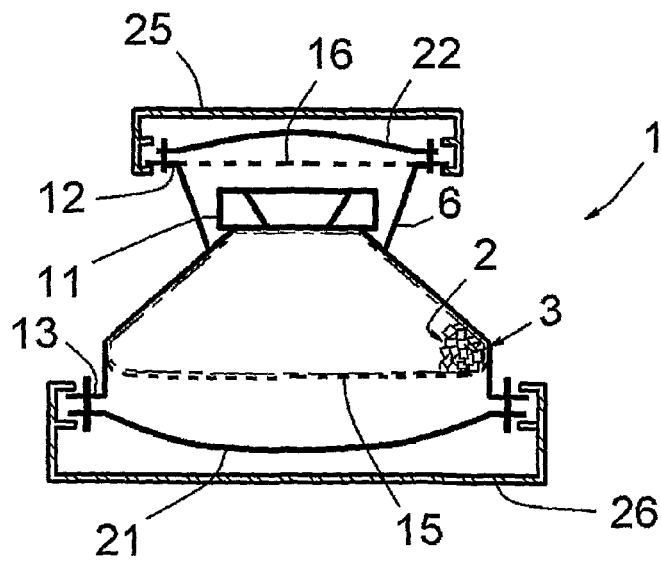
FIG. 6 is a similar view of the packing, in its final constitution.

FIG. 6 illustrates a packing 1 intended to contain one or several objects 2, in particular component parts of syringes, and in particular syringe plungers. These objects 2 fully fill a container 3 comprised by the packing 1 but, out of a concern for clarity in the drawing, they have been illustrated only partially: the contour of the assembly formed by these objects 2 is defined by a dashed line.

Figure 1:
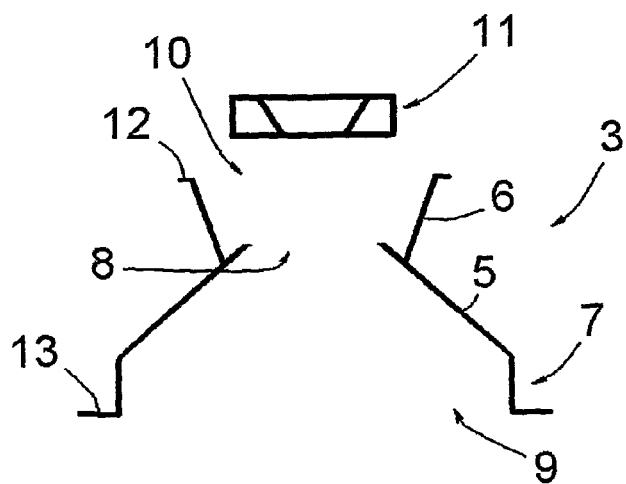
FIGS. 1 to 3 are very simplified cross-sectional views of different component pieces of this packing and of objects contained in this packing, during three successive steps of making up this packing.

As shown by FIG. 1, the container 3 comprises a rigid body 5 intended to receive the objects 2, a flange 6 and a base 7. The assembly can be formed in a single piece of material, in particular in a plastic material able to resist sterilization in particular by water vapor.

The body 5 has a truncated shape and comprises upper 8 and lower 9 openings located at its ends having the smallest and largest cross-section, respectively.

The flange 6 is integral with the body 5 and is made up of a peripheral wall, defining an upper opening 10. It forms an envelope able to completely contain a connection ring 11 and comprises a terminal outside peripheral rim 12 constituting a seat for the later sealing of a membrane.

The base 7 is formed by an outside peripheral rim 13 comprised by the body 5.

Figure 2:
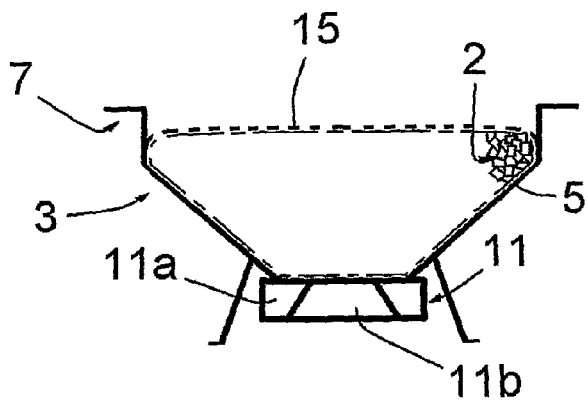

As shown by FIG. 2, the connection ring 11 is designed to be placed on the opening 8 and to be fixed to the body 5. This ring comprises a circular base 11a defining an opening for discharging of the objects 2 and a removable door 11b which, at this stage of use of the packing 1, closes this discharge opening. This ring 11 is for example of the type described in documents U.S. Pat. Nos. 6,571,540 and 6,817,143, and therefore will not be described in further detail.

After fixing of the connection ring 11 to the body 5, the container 3 is returned and filled with objects 2, up to a level located set back from the base 7. A membrane 15 made of a material porous to a sterilization fluid but not porous to microbial contamination is then sealed on all of the periphery of the wall of the body 5, set back from the base 7, so as to close the opening 9.

This membrane 15 comprises pores whereof the size can go from 2 to 15 microns and a Log Reduction Value (as defined in the ASTM F-1608 standard) greater than or equal to 3. This can be a film marketed by the company Du Pont De Nemours under the TYVEK® brand, references 1073B, 2FS or 1059B, or a complex marketed by the company WIPAK under the WIPAK® brand, references Paper 80B or Paper 120B.

Figure 3:
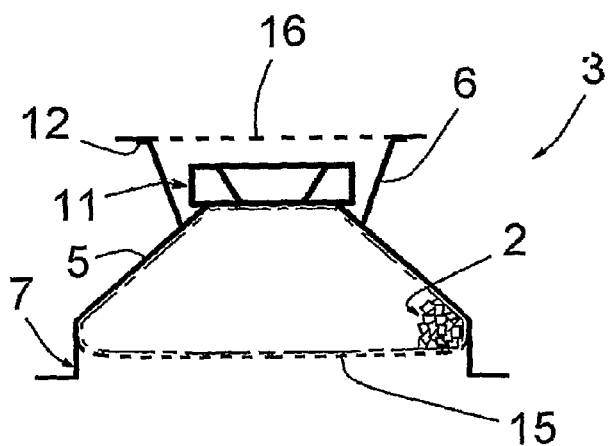

The container 3 is then returned, then, as visible in FIG. 3, another membrane 16 is sealed on all of the periphery of the rim 12 so as to close the opening 10 defined by the flange 6. This membrane 16 is also made of a material porous to a sterilization fluid but not porous to microbial contamination, and can in particular be made of the same material as the membrane 15.

Figure 4:
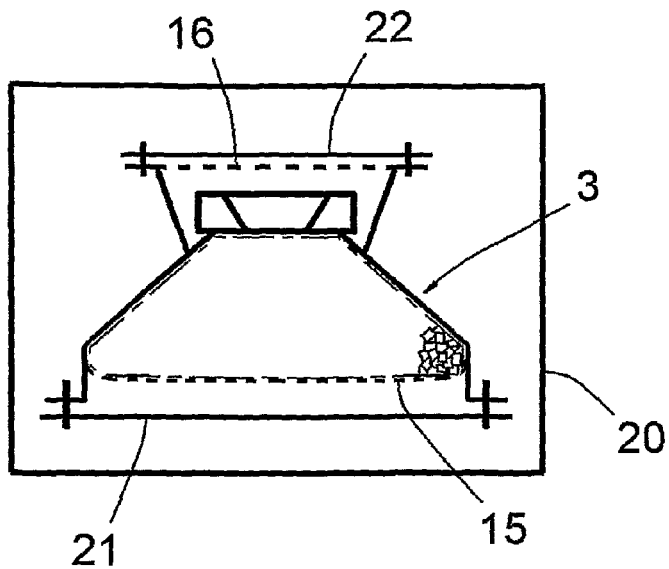
FIG. 4 is a similar view of different component parts of the packing, placed in a sterilization enclosure.
Figure 5:
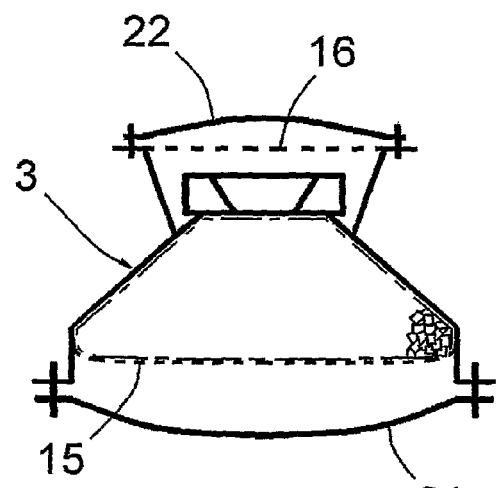
FIG. 5 is a similar view of different component parts of the packing after sterilization.

The assembly thus formed is, as shown in FIG. 4, placed in a sterilization enclosure 20. This enclosure 20 contains a sterilization fluid, in particular water vapor, under a pressure higher than the atmospheric pressure. After sufficient exposure of this assembly to the sterilization fluid to perform the sterilization of the objects 2, and while the enclosure 20 is kept under a pressure higher than the atmospheric pressure, the container 3 receives two other membranes 21, 22, made of a flexible and airtight material. These membranes 21, 22 completely cover the membranes 15 and 16 and are respectively sealed to these membranes as well as to the rims 12 and 13, on all of the periphery of these rims.

When the assembly is removed from the enclosure 20, and it is therefore brought back to the atmospheric pressure, the membranes 21, 22 assume a curved shape, as shown in FIG. 6.

This assembly then receives two transparent lids 25, 26 (cf. FIG. 6), comprising peripheral rims allowing their clipping onto the rims 7 and 13 and on the membranes 15, 21 and 16, 22, these lids 25, 26 being dimensioned to cover the membranes 21, 22 in the curved state thereof.

The packing 1 thus uses membranes 15, 16 whereof the porosity allows a sufficient diffusion of the sterilization fluid inside the container 3 and around the objects 2; the tight sealing of these membranes on the container 3 makes it possible to preserve the integrity of the sterilization performed for the objects 2, the internal wall of the container 3 and the internal wall of these membranes.

The rigidity of the container 3 makes it possible to preserve the integrity of the objects 2 with regard to the mechanical stresses likely to be exerted on these objects in particular during the transport thereof, which is necessary when these objects are liable to be deformed or damaged under the prolonged exertion of such mechanical stresses, as is the case for example for syringe plungers. This rigidity also has the advantage of granting a fixed shape to the set of objects, optimized for a homogenous exposure to the sterilization fluid, which is a crucial parameter for sterilization using water vapor. In other words, the rigid container makes it possible to eliminate any pile of objects which would be made possible with a flexible container, causing a risk of the sterilization fluid not sufficiently penetrating to the center of this pile to ensure the required sterilization. The rigidity of the container also has the advantages of making it possible to increase the capacity of a packing relative to the maximum capacity a known flexible packing can have, and to facilitate the treatments and manipulations done by the operations.

The curving of the membranes 21, 22 indicates the absence of air having escaped from the inside of the packing, and therefore indicates the preservation of the sterility thereof.

The lids 25, 26 ensure the protection of the membranes 21, 22 with regard to a risk of crushing or exertion of stretching stresses on these membranes, and enable visualization of the shape of these membranes through them. The integrity of these membranes can thus be verified without it being necessary to remove these lids.

As appears from the preceding, the invention provides a sterile packing and a sterilization method using this packing, having the determining advantages of allowing effective sterilization of objects by the sterilization fluid, perfectly protecting the packed object(s) with regard to the environment, and enabling an immediate indication of any loss of integrity, and therefore of sterility, of the packing.

It must be specified that the embodiment of the invention described above was provided purely as an example. It goes without saying that the invention is not limited to this embodiment, but that it extends to all embodiments covered by the appended claims.

The invention claimed is:

1. Sterile packing, including:
   a container for containing at least an object to be sterilized by at least a sterilizing fluid, said container including at least one first opening;
   at least one first membrane made in a material porous to the sterilizing fluid but non-porous with respect to microbial contamination, said at least one first membrane being sealed at said at least one first opening of the container, after filling of the container with the object so as to close said at least one first opening;
   at least one second membrane made in a flexible and airtight material, said at least one second membrane being sealed at said at least one first opening of the container,
   wherein, said at least one second membrane is sealed at said at least one first opening after, and separate from, installation of said at least one first membrane at said at least one first opening, the sealing of said at least one second membrane being carried out at a pressure higher than the atmospheric pressure, so that said at least one second membrane is curved when the packing is brought back to the atmospheric pressure.

2. Sterile packing according to claim 1, wherein said container includes a second opening set back from said at least one first opening, interiorly of the container, and wherein said package includes a connection ring for connection to a sterile enclosure in which the object to be packed is intended to be transferred, said connection ring being connected to said second opening.

3. Sterile packing according to claim 2, wherein the container defines an envelope suitable to contain the connection ring and forming a seat for the sealing of said at least one first membrane.

4. Sterile packing according to one of claims 1 to 3, wherein the container includes at least one third opening located at an end opposite of said end at which said at least one first opening is located, a second of said at least one first membrane being sealed at said at least one third opening of the container, after filling of the container with the object so as to close said at least one third opening.

5. Sterile packing according to claim 4, wherein a second one of said at least one second membrane is sealed at said at least one third opening of the container, after filling of the container with the object so as to close said at least one third opening, the sealing of said second one of said at least one second membrane being carried out at a pressure higher than the atmospheric pressure, so that said at least one second membrane at said at least one third opening is curved when the packing is brought back to the atmospheric pressure.

6. Sterile packing according to claim 5, further comprising at least one lid able to cover at least one of said second membranes, in the curved state of said second membrane.

7. Sterile packing according to claim 6, wherein each said lid is totally or partially transparent.

8. Sterile packing according to claim 4, wherein the container has a truncated form or a truncated pyramid form, said at least one first opening, or, when said connection ring is present, said second opening, being located at the small section end of said container and said at least one third opening being located at the base of said container.

9. Sterile packing according to claim 8, wherein the base of said container is formed by an outside peripheral rim, said at least one first membrane being sealed at said at least one third opening set back from the base, interiorly of the container.

10. Sterile packing according to claim 1, wherein the container includes a discharge conduit for discharging the objects, able to be engaged through the opening of said container used for discharging the objects out of said container.

11. Sterile packing according to claim 1, wherein said at least one first membrane is made of a plurality of layers.

12. Sterile packing according to claim 1, wherein said container is rigid.

13. Sterilization process, using a sterile packing according to claim 1, including the steps comprising:
- filling the container with said at least one object to be sterilized;
- sealing said at least one first membrane at said at least one first opening;
- simultaneously or not to the sealing of said at least one first membrane, sterilizing said at least one object;
- generating a pressure higher than the atmospheric pressure about the container with said at least one first membrane sealed at said at least one first opening; then
- sealing said at least one second membrane at said at least one first opening wherein said pressure higher than the atmospheric pressure is maintained, so that said at least one second membrane is curved when the packing is brought back to the atmospheric pressure.

* * * * *

UNITED STATES PATENT AND TRADEMARK OFFICE
CERTIFICATE OF CORRECTION

PATENT NO. : 8,679,419 B2  
APPLICATION NO. : 12/996640  
DATED : March 25, 2014  
INVENTOR(S) : Mermet et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 552 days.

Signed and Sealed this

Twenty-ninth Day of September, 2015

Michelle K. Lee  
*Director of the United States Patent and Trademark Office*